(12) United States Patent  
Besancon

(10) Patent No.: US 8,932,244 B1  
(45) Date of Patent: Jan. 13, 2015

(54) ANIMAL SPINAL DECOMPRESSION BRACE

(76) Inventor: Mark A. Besancon, Victoria, TX (US)

(*) Notice: Subject to any disclaimer, the term of this patent is extended or adjusted under 35 U.S.C. 154(b) by 46 days.

(21) Appl. No.: 13/464,761

(22) Filed: May 4, 2012

Related U.S. Application Data

(60) Provisional application No. 61/482,651, filed on May 5, 2011.

(51) Int. Cl.  
*A61F 5/00* (2006.01)

(52) U.S. Cl.  
USPC .............................. 602/19; 119/856; 119/907

(58) Field of Classification Search  
USPC ............ 602/5, 12, 16, 19; 119/727, 728, 856, 119/907; 5/625, 627, 628  
See application file for complete search history.

(56) References Cited

U.S. PATENT DOCUMENTS

| | | | | |
|---|---|---|---|---|
| 4,286,547 | A * | 9/1981 | Nuwbauer et al. | 119/815 |
| 5,924,388 | A * | 7/1999 | Peeples | 119/814 |
| 6,450,926 | B1 * | 9/2002 | McKernan | 482/91 |
| 6,976,453 | B2 * | 12/2005 | Goudal | 119/815 |

* cited by examiner

*Primary Examiner* — Michael A. Brown  
(74) *Attorney, Agent, or Firm* — Michael J. Neuerburg

(57) ABSTRACT

A wearable device for spinal decompression of dogs or other quadrupedal animals. The preferred embodiment of the device comprises front and rear harnesses of flexible material extending around the animal's torso, curved members attached to the front and rear harnesses and lying along the animal's body, and rigid extensible braces connected to the front and rear curved members, generally parallel to the animal's spine. The harnesses, braces, and curved members are selected or can be adjusted to fit the animal. The extensible rods are adjustable, with means to produce therapeutic decompression and support of the animal's spine between the front and rear harnesses.

13 Claims, 2 Drawing Sheets

ANIMAL SPINAL DECOMPRESSION BRACE

BACKGROUND OF THE INVENTION

This invention relates to animal spinal braces, and more particularly to wearable devices which exert a decompressive force on the spine of a quadrupedal animal.

Studies have shown that decompression of the spine can have a beneficial medical effect in the treatment of spinal maladies. Spinal decompression therapy for humans typically involves the regular use of a large, stationary device which immobilizes the patient and applies decompressive force to the spine. However, while it is possible to persuade humans to lie quietly and still in such a device, most animals are not so compliant. Thus, due to the relative difficulty of immobilizing animals, it is desirable that a device for spinal decompression of animals be wearable.

PRIOR ART

Document U.S. Pat. No. 6,976,453 describes a device for restricting an animal's movement. It includes various front and rear harness configurations, connected by rigid means for restricting the animal's movement. Though the device can be used to restrict movement of the spine, it has no means of providing therapeutic decompression of the spine.

Document U.S. Pat. No. 2,835,247 describes a wearable device for spinal decompression in humans. It includes upper and lower harnesses and manually extended force transmitting rods.

Document U.S. Pat. No. 5,462,518 describes a wearable device for spinal decompression in humans. It includes no upper harness and applies the decompressive force entirely to the patient's arms.

Document U.S. Pat. No. 6,997,892 describes a wearable device for spinal decompression in humans. It applies the decompressive force to a specific point on the patient's spine. It employs powered lifting devices to apply decompressive force at specific time intervals.

SUMMARY OF THE INVENTION

It is an object of this invention to provide an animal brace which is wearable by the animal and which exerts a decompressive force on the spine of the animal. Another object of the invention is to be adjustable, so that it can be fitted to the individual animal or used on other animals of similar size. Yet another object of the invention is to provide therapeutic decompression of the animal's spine without unduly interfering with the animal's movement or comfort. Yet another object of the invention is to leave space around the animal's spine to as not to interfere with any surgical incisions and to permit bandaging or care of such incisions. Yet another object of the invention is to be simple in operation, such that it can be applied to the animal or removed from the animal by the animal's owner.

These and other objects are realized by a wearable animal spinal decompression device. The device comprises forward and rear harnesses connected by extensible braces. The forward harness may be comprised of a strip of flexible material having first and second ends, said first and second ends having an adjustable means by which they can attach to each other, such that the forward harness can be made to encircle the chest of the animal caudal to the animal's forelimbs with said adjustable attachment means adjusted so that the harness fits snugly. Similarly, the rear harness may be comprised of a strip of flexible material having first and second ends, said first and second ends having an adjustable means by which they can attach to each other, such that the rear harness can be made to encircle the waist of the animal cranial to the animal's hind limbs with said adjustable attachment means adjusted so that the harness fits snugly. It is preferable that the front and rear harnesses be padded for the animal's comfort.

Each extensible brace is disposed between the front and rear harnesses, generally parallel to the animal's spine, the front end of each extensible brace being connected to the front harness, and the rear end of each extensible brace being connected to the rear harness. Each extensible brace includes means for creating a decompressive force between the front and rear harnesses. Preferably, each extensible brace will include means for applying such decompressive force at the animal's shoulders and hips and distributing such decompressive force for the animal's comfort. Preferably, each extensible brace will comprise a forward curved member, a rear curved member, and an extensible connecting member having forward and rear ends. The extensible connecting members are disposed on each side of the animal, generally parallel to the animal's torso. Each forward curved member is attached in a generally perpendicular fashion to the forward end of the corresponding extensible connecting member, such that each forward curved member lies along the forward harness at the animal's ribcage, curving from the extensible connecting member attachment point at the animal's side, under the animal's foreleg, and toward the animal's breastbone. Similarly, each rear curved member is attached in a generally perpendicular fashion to the rear end of an extensible connecting member, such that each rear curved member lies along the rear harness at the animal's waist, curving from the extensible connecting member attachment point at the animal's side toward the animal's ventral surface. That is, when the invention is placed on the animal, the curvature of each curved member is generally within the animal's transverse plane with the center of curvature being toward the animal, and the extensible connecting member oriented generally parallel to the animal's spine. Each extensible connecting member is generally straight and rigid and includes a means by which it may be lengthened or shortened.

The means for adjusting an extensible connecting member is preferably comprised of two oppositely threaded lengths of metal rod connected by a threaded coupling, such that rotation of the threaded coupling in one direction causes the extensible connecting member to lengthen, while rotation of the threaded coupling in the other direction causes shortening of the extensible connecting member. It is preferable to include locking nut or other mechanism to prevent unwanted or accidental adjustment of the extensible connecting member.

DESCRIPTION OF THE DRAWINGS

The features, objects, and advantages of the invention will be more easily understood by reading the following description of the preferred embodiment of the invention in conjunction with the accompanying drawings.

DESCRIPTION OF THE PREFERRED EMBODIMENT AND BEST MODE OF USE

Figure 1:
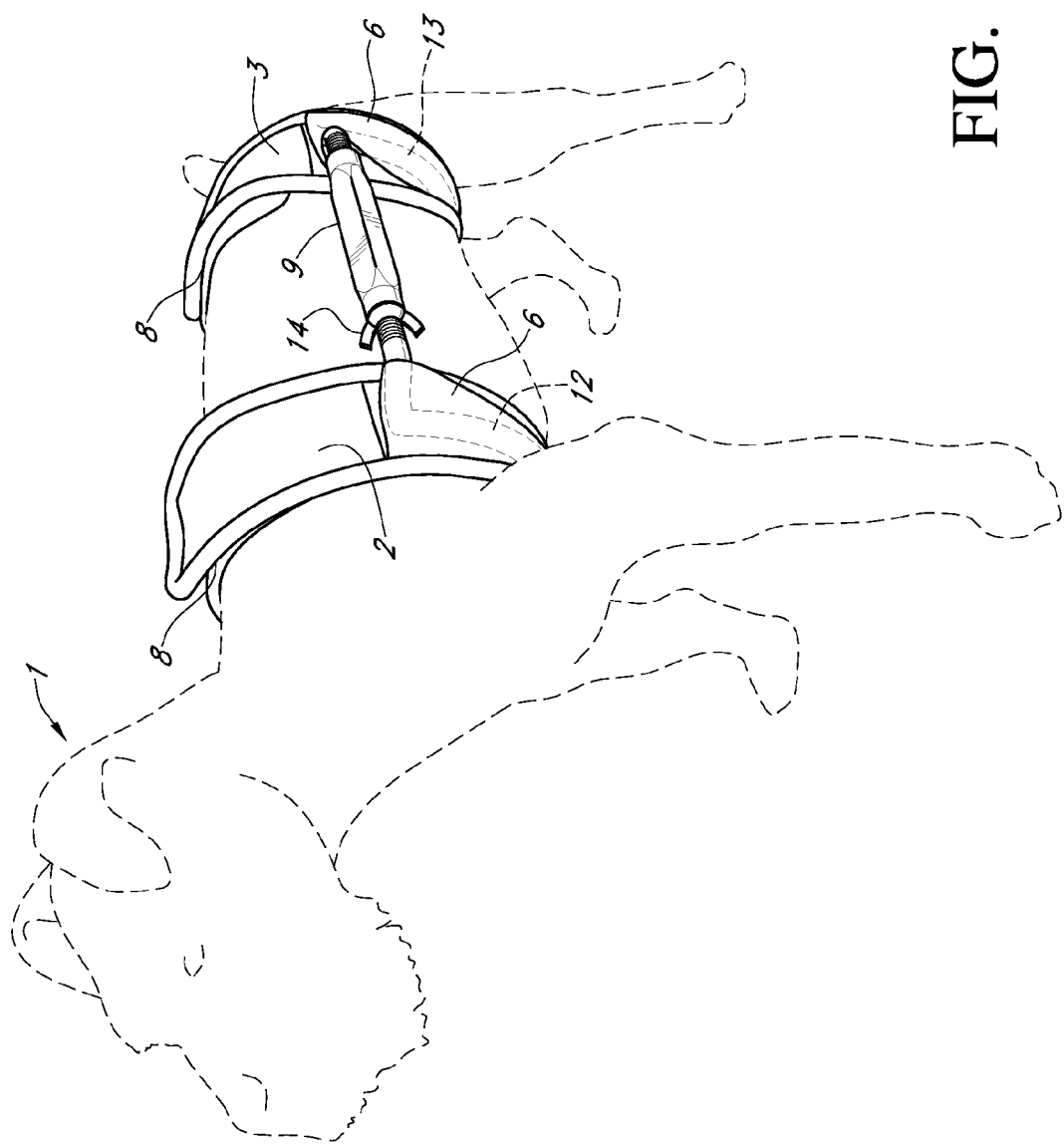
FIG. 1 shows the preferred embodiment of the invention in use on a dog.
Figure 2:
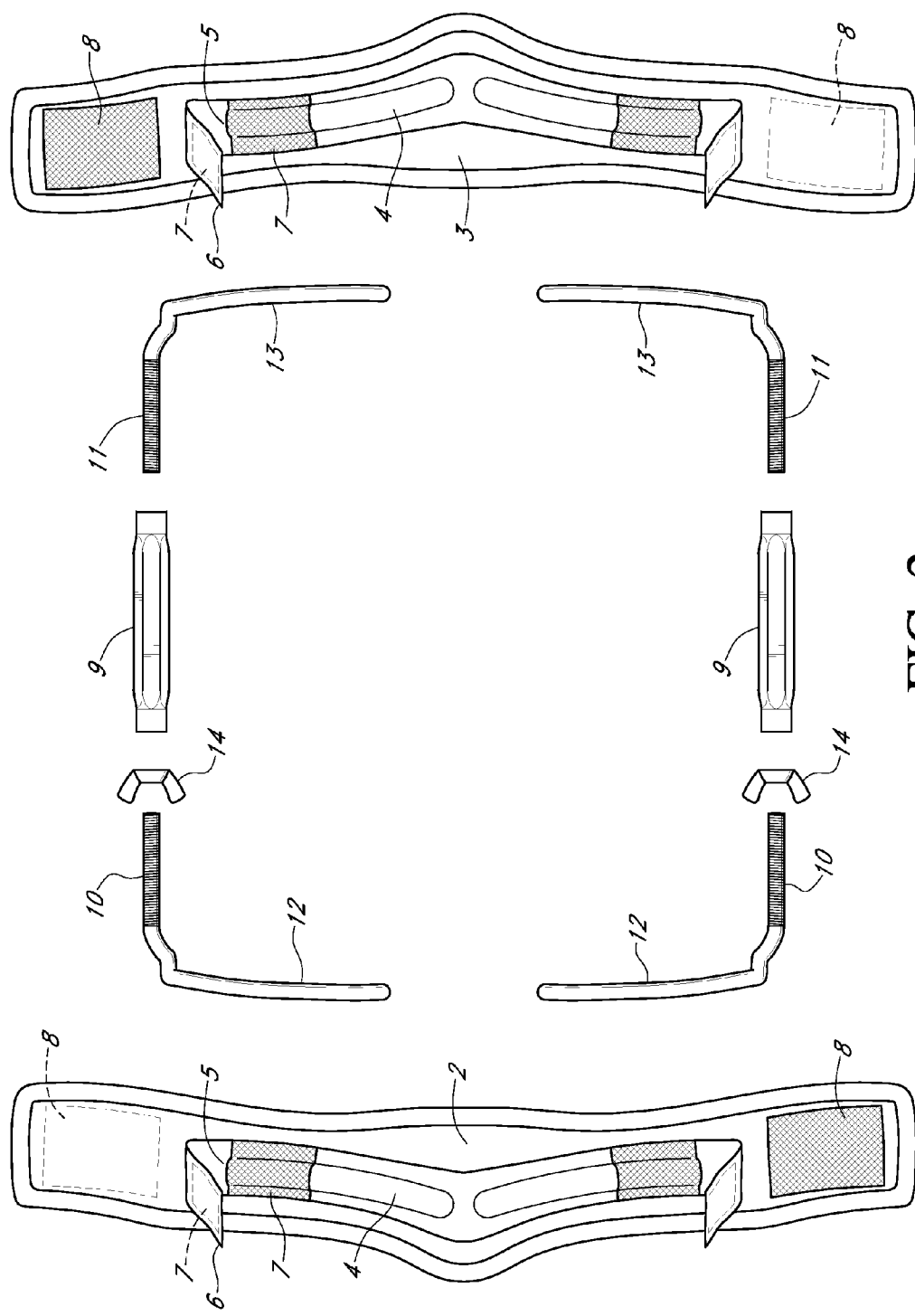
FIG. 2 is an exploded view of the preferred embodiment, showing the parts of the invention.

The forward harness 2 and rear harness 3 are flexible strips which each encircle the animal 1. It is preferable that the surface of the harness in contact with the animal be padded for the animal's comfort. A material such as foamed neoprene has been found to be suitable for padding. Attached to the exterior surface of each harness are two long, narrow pockets 4 formed of flexible material. The pockets 4 are positioned such that on each harness, one pocket is on each side of the animal 1, with each pocket having its opening 5 at the animal's side and extending along the harness in a ventral direction. A cover flap 6 comprising a strip of flexible material and fastening means 7 is attached by one endpoint just above the opening 5 of each pocket 4 such that the cover flap can be laid over the pocket and secured to cover the pocket opening, or laid away from the pocket to provide access to the pocket. Velcro has been found to be a suitable fastener 7 for securing the cover flaps 6 over the pockets 4. Velcro has also been found to be suitable as an adjustable fastener 8 for adjustably fastening the endpoints of a harness 2, 3 together so that the harness snugly encircles the animal.

In the preferred embodiment each extensible brace is comprised of a threaded coupling 9, a forward threaded rod 10, a rear threaded rod 11, a forward curved member 12, and a rear curved member 13. Aluminum has been found to be a suitable material for these components. Other stiff materials would be suitable, though light materials are preferred for the comfort of the animal, particularly for small animals. Should there be a possibility of the invention coming into contact with medication, or concerns regarding the sterilization of the invention, a non-reactive material such as stainless steel would be suitable for the brace. The forward threaded rods 10 and rear threaded rods 11 are threaded in opposite directions, with the threaded coupling 9 correspondingly threaded at each end. The forward and rear threaded rods are joined by the threaded coupling. Thus, rotating the threaded coupling causes the threaded rods to travel longitudinally in opposite directions, either lengthening or shortening the extensible brace. A locking nut 14 is placed on a threaded rod on each side prior to attaching the threaded coupling, such that tightening the locking nut 14 onto the threaded coupling 9 prevents the threaded coupling from being turned. One end of the forward curved member 12 is fixedly attached generally perpendicular to the uncoupled end of the forward threaded rod 10; it is preferable that the other end be rounded or tapered so as to slide easily into a pocket 4 on the forward harness 2. Similarly, one end of the rear curved member 13 is fixedly attached generally perpendicular to the uncoupled end of the rear threaded rod 11; it is preferable that the other end be rounded or tapered so as to slide easily into a pocket 4 on the rear harness 3.

Naturally, the size of the various components of the invention may be altered to fit the animal. A larger animal may require that the components be larger and capable of exerting a greater decompressive force. The configuration of the components may also be altered to fit the animal. For example, attaching the forward and rear curved members at a slight outward angle, such that the forward curved members 12 point in a slightly cranial direction and the rear curved members 13 point in a slightly caudal direction, has been found especially effective in applying the decompressive force in some dogs.

The following procedure has been found to be most effective for the use of the preferred embodiment of the invention: The forward harness 2 is fitted snugly around the animal's 1 chest, just caudal to the animal's forelimbs. The rear harness 3 is fitted snugly around the animal's waist, just cranial to the animals hind limbs. The extensible braces are assembled by joining the forward curved member 12 to the forward threaded rod 10, joining the rear curved member 13 to the rear threaded rod 11, placing the locking nut 14 on the appropriate threaded rod, and joining the forward and rear threaded rods 10, 11 with the threaded coupling 9. By rotating the threaded coupling 9, the extensible braces are adjusted to a length approximately equal to the distance between harnesses 2, 3. The extensible braces are then attached to the harnesses by inserting the forward curved member 12 of each extensible brace into the corresponding pocket 4 on the forward harness and inserting the rear curved member 13 of each extensible brace into the corresponding pocket 4 on the rear harness. The extensible braces are secured in place by securing the cover flaps 6 over the pockets 4. With the invention secured to the animal, the threaded couplings 9 are then turned so as to extend the extensible braces. This extension exerts a decompressive force on the animal's spine. When the desired amount of extension is reached, the lock nuts 14 are turned into place against the threaded coupling 9, locking the threaded coupling in place. These steps are performed in reverse to remove the invention. A veterinarian or other specialist may mark the location of the threaded coupling 9 on the threaded rods 10, 11 at the desired amount of extension; thereafter the invention may be fitted by the animal's owner by turning the threaded coupling 9 to the marked location.

Alternative Embodiments

Variations and modifications, including those described below, may be made without departing from the scope of the invention. One possible modification would be to incorporate more extensible braces. Another possible modification would be to incorporate additional harnesses or supports secured to the extensible braces between the forward and rear harnesses. Yet another possible modification would be to replace the threaded rods and couplings in the extensible braces with compression springs or similar elastic means of providing an extending force. Such compression springs could be adjusted to modify the decompressive force; alternatively, the decompressive force could be modified by exchanging the particular spring or other elastic means with a spring or elastic means of more or less elasticity. Yet another possible modification would be to use alternative attachment means to secure the harnesses on the animal, or to secure the extensible braces to the harnesses. Yet another possible modification would be to include a means to stiffen the harnesses to distribute the decompressive force from the extensible brace. Yet another possible modification would be to use alternative locking means to prevent movement of an extensible brace once it is adjusted to the desired length. Yet another possible modification would be to add attachment points so that additional veterinary devices, such as a hind leg support cart or neck brace, could easily be attached to the invention.

What is claimed is:

1. A wearable device for spinal decompression of animals comprising:
   a first harness, said harness adjustable so as to encircle the chest of the animal just caudal of the animal's forelegs;
   a second harness, said harness adjustable so as to encircle the waist of the animal just cranial of the animal's rear legs;
   one or more extensible braces disposed generally parallel with each other and with the animal's spine, wherein each extensible brace is comprised of an extensible connecting rod having first and second ends, a first curved member, and a second curved member; where said the first end of said extensible connecting rod is attached to said first curved member, said first curved member is attached to said first harness and curved to fit closely to the animal's chest, the second end of said extensible connecting rod is attached to said second curved member, and said second curved member is attached to said second harness and curved to fit closely to the animal's waist, and such extensible braces being formed of material sufficiently strong and rigid to transmit the desired decompressive force between the first and second harnesses; and means for producing a decompressive force between said first and second ends of each extensible brace.

2. An animal spinal decompression device as set out in claim 1, in which at least two extensible braces are used, wherein the first curved member of the first extensible brace lies along the animal's chest just caudal of the shoulder joint of the animal's left foreleg, the second curved member of the first extensible brace lies along the animal's waist just cranial of the hip joint of the animal's left rear leg, the first curved member of the second extensible brace lies along the animal's chest just caudal of the animal's right foreleg, and the second curved member of the second extensible brace lies along the animal's waist just cranial of the hip joint of the animal's right rear leg.

3. An animal spinal decompression device as set out in claim 2, in which the means by which each curved member is attached to its corresponding harness comprises a pocket attached to the harness in which the curved member is inserted, and fastening means to hold the curved member in the pocket.

4. An animal spinal decompression device as set out in claim 2, additionally comprising cushioning material between the animal and the curved members.

5. A wearable device for spinal decompression of animals comprising:
   a first harness, said harness adjustable so as to encircle the chest of the animal just caudal of the animal's forelegs;
   a second harness, said harness adjustable so as to encircle the waist of the animal just cranial of the animal's rear legs;
   one or more extensible braces, each having first and second ends, disposed generally parallel with each other and with the animal's spine, said first ends of the extensible braces being connected to the first harness, and said second ends of the extensible braces being connected to the second harness, and such extensible braces being formed of material sufficiently strong and rigid to transmit the desired decompressive force between the first and second harnesses; and
   means for producing a decompressive force between said first and second ends of each extensible brace comprising a first rod with external threading, a second rod with external threading opposite to the threading on said first rod, and a threaded coupling having first and second end, said first end having internal threading to match the threading of said first rod and said second end having threading to match the threading of said second rod, with said first rod threaded into said first end of the threaded coupling and said second rod threaded into said second end of the threaded coupling such that rotating the threaded coupling causes the first and second threaded rods to travel in opposite linear directions.

6. An animal spinal decompression device as set out in claim 5, additionally comprising a locking means for preventing unintended rotation of each threaded coupling.

7. An animal spinal decompression device as set out in claim 5, wherein each extensible brace is comprised of an extensible connecting rod having first and second ends, a first curved member, and a second curved member; where said the first end of said extensible connecting rod is attached to said first curved member, said first curved member is attached to said first harness and curved to fit closely to the animal's chest, the second end of said extensible connecting rod is attached to said second curved member, and said second curved member is attached to said second harness and curved to fit closely to the animal's waist.

8. An animal spinal decompression device as set out in claim 7, in which at least two extensible braces are used, wherein the first curved member of the first extensible brace lies along the animal's chest just caudal of the shoulder joint of the animal's left foreleg, the second curved member of the first extensible brace lies along the animal's waist just cranial of the hip joint of the animal's left rear leg, the first curved member of the second extensible brace lies along the animal's chest just caudal of the animal's right foreleg, and the second curved member of the second extensible brace lies along the animal's waist just cranial of the hip joint of the animal's right rear leg.

9. An animal spinal decompression device as set out in claim 8, in which the means by which each curved member is attached to its corresponding harness comprises a pocket attached to the harness in which the curved member is inserted, and fastening means to hold the curved member in the pocket.

10. An animal spinal decompression device as set out in claim 8, additionally comprising cushioning material between the animal and the curved members.

11. A wearable device for spinal decompression of animals comprising:
    a first harness, said harness adjustable so as to encircle the chest of the animal just caudal of the animal's forelegs;
    a second harness, said harness adjustable so as to encircle the waist of the animal just cranial of the animal's rear legs;
    one or more extensible braces, each having first and second ends, disposed generally parallel with each other and with the animal's spine, said first ends of the extensible braces being connected to the first harness, and said second ends of the extensible braces being connected to the second harness, and such extensible braces being formed of material sufficiently strong and rigid to transmit the desired decompressive force between the first and second harnesses;
    means for producing a decompressive force between said first and second ends of each extensible brace; and
    one or more pieces of flexible material for the support of the animal's torso and abdomen, with one end of such pieces of flexible material attached to an extensible brace on one side of the animal, the middle of such pieces of flexible material passing under the animal's torso and/or abdomen and the other opposite end of such pieces of flexible material connecting to an extensible brace on the other side of the animal.

12. A wearable device for spinal decompression of animals comprising:
    a first harness, said harness adjustable so as to encircle the neck of the animal just caudal of the animal's head;
    a second harness, said harness adjustable so as to encircle the chest of the animal;
    means to prevent said second harness from sliding caudally;
    one or more extensible braces, each having first and second ends, disposed generally parallel with each other and with the animal's spine, said first ends of the extensible braces being connected to the first harness, and said second ends of the extensible braces being connected to the second harness, and such extensible braces being formed of material sufficiently strong and rigid to transmit the desired decompressive force between the first and second harnesses; and means for adjusting the length of said extensible braces comprising a first rod with external threading, a second rod with external threading opposite to the threading on said first rod, and a threaded coupling having first and second end, said first end having internal threading to match the threading of said first rod and said second end having threading to match the threading of said second rod, with said first rod threaded into said first end of the threaded coupling and said second rod threaded into said second end of the threaded coupling such that rotating the threaded coupling causes the first and second threaded rods to travel in opposite linear directions.

13. A wearable device for spinal decompression of animals comprising:

a first harness, said harness adjustable so as to encircle the chest of the animal just caudal of the animal's forelegs;

a second harness, said harness adjustable so as to encircle the waist of the animal just cranial of the animal's rear legs;

one or more extensible braces, each having first and second ends, disposed generally parallel with each other and with the animal's spine, said first ends of the extensible braces being connected to the first harness, and said second ends of the extensible braces being connected to the second harness, and such extensible braces being formed of material sufficiently strong and rigid to transmit the desired decompressive force between the first and second harnesses;

means for producing a decompressive force between said first and second ends of each extensible brace; and a force sensor to measure the decompressive force applied to the animal.

* * * * *